US00PP32200P2

(12) United States Plant Patent
Holtmaat

(10) Patent No.: US PP32,200 P2
(45) Date of Patent: Sep. 15, 2020

(54) ***ANEMONE* PLANT NAMED 'ANEM079'**

(50) Latin Name: *Anemone multifida x Anemone sylvestris*
Varietal Denomination: ANEM079

(71) Applicant: Henricus Maria Joseph Holtmaat, Zuidwolde (NL)

(72) Inventor: Henricus Maria Joseph Holtmaat, Zuidwolde (NL)

(73) Assignee: Nova Perenne B.V., Zuidwolde (NL)

( * ) Notice: Subject to any disclaimer, the term of this patent is extended or adjusted under 35 U.S.C. 154(b) by 0 days.

(21) Appl. No.: 16/501,900

(22) Filed: Jul. 1, 2019

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 6/72
See application file for complete search history.

(56) References Cited

PUBLICATIONS

UPOV hit on *Anemone* plant named 'ANEM079', QZ PBR 20190348, filed Feb. 1, 2019.*

* cited by examiner

*Primary Examiner* — Anne Marie Grunberg
(74) *Attorney, Agent, or Firm* — C. A. Whealy

(57) ABSTRACT

A new and distinct cultivar of *Anemone* plant named 'ANEM079', characterized by its upright plant habit; moderately vigorous growth habit; freely flowering habit; relatively large single-type flowers that are purple in color; and good garden performance.

2 Drawing Sheets

Botanical designation: *Anemone multifida* x *Anemone sylvestris.*
Cultivar denomination: 'ANEM079'.

CROSS-REFERENCED TO CLOSELY RELATED APPLICATIONS

Title: *Anemone* Plant Named 'ANEM078'
Applicant: Henricus Maria Joseph Holtmaat
Filed: Concurrently with this application having application Ser. No. 16/501,897

BACKGROUND OF THE INVENTION

The present invention relates to a new and distinct cultivar of *Anemone*, botanically known as *Anemone multifida* x *Anemone sylvestris* and hereinafter referred to by the name 'ANEM079'.

The new *Anemone* plant is a product of a planned breeding program conducted by the Inventor in Zuidwolde, The Netherlands. The objective of the breeding program is to create new freely-flowering *Anemone* plants with large attractive flowers.

The new *Anemone* plant originated from a cross-pollination made by the Inventor in April, 2016 in Zuidwolde, The Netherlands of *Anemone multifida* 'Rosea', not patented, as the female, or seed, parent with an unnamed selection of *Anemone sylvestris*, not patented, as the male, or pollen, parent. The new *Anemone* plant was discovered and selected by the Inventor as a single flowering plant within the progeny of the stated cross-pollination in a controlled greenhouse environment in Zuidwolde, The Netherlands in April, 2018.

Asexual reproduction of the new *Anemone* by in vitro meristem culture in a controlled environment in Zuidwolde, The Netherlands since November, 2018 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'ANEM079'. These characteristics in combination distinguish 'ANEM079' as a new and distinct *Anemone* plant:

1. Upright plant habit.
2. Moderately vigorous growth habit.
3. Freely flowering habit.
4. Relatively large single-type flowers that are purple in color.
5. Good garden performance.

Plants of the new *Anemone* can be compared to plants of the female parent, 'Rosea'. Plants of the new *Anemone* differ primarily from plants of 'Rosea' in the following characteristics:

1. Plants of the new *Anemone* are taller than plants of 'Rosea'.
2. Plants of the new *Anemone* are more freely flowering than plants of 'Rosea'.

Plants of the new *Anemone* can be compared to plants of the male parent selection. Plants of the new *Anemone* differ primarily from plants of the male parent selection in the following characteristics:

1. Plants of the new *Anemone* are taller than plants of the male parent selection.
2. Leaves of plants of the new *Anemone* are shorter than leaves of plants of the male parent selection.
3. Plants of the new *Anemone* have purple-colored flowers whereas plants of the male parent selection have pure white-colored flowers.

Plants of the new *Anemone* can be compared to plants of *Anemone multifida* 'Annabella Deep Rose', not patented. In side-by-side comparisons, plants of the new *Anemone* and 'Annabella Deep Rose' differ primarily in the following characteristics:

1. Plants of the new *Anemone* have longer stems than plants of 'Annabella Deep Rose'.
2. Plants of the new *Anemone* have larger flowers than plants of 'Annabella Deep Rose'.

Plants of the new *Anemone* can be compared to plants of *Anemone multifida* x *Anemone sylvestris* 'ANEM078', disclosed in a U.S. Plant Patent application filed concurrently having application Ser. No. 16/501,897. In side-by-side comparisons, plants of the new *Anemone* and 'ANEM078' differ primarily in flower color as plants of the new *Anemone* have purple-colored flowers whereas plants of 'ANEM078' have light yellow green to white-colored flowers. In addition, plants of the new *Anemone* are smaller and have fewer branches and flowers than plants of 'ANEM078'.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'ANEM079' grown in a container.

The photograph at the top of the second sheet comprises a close-up view of a typical leaf of 'ANEM079'.

The photograph at the bottom of the second sheet comprises a close-up view of typical flowers of 'ANEM079'.

DETAILED BOTANICAL DESCRIPTION

The aforementioned photographs and following observations, measurements and values describe plants grown during the spring in 17-cm containers in an outdoor nursery in Zuidwolde, The Netherlands and under cultural practices typical of commercial *Anemone* production. During the production of the plants, day temperatures ranged from 18° C. to 30° C. and night temperatures ranged from 6° C. to 18° C. Plants were eight months old when the photographs and description were taken. In the following description, color references are made to The Royal Horticultural Society Colour Chart, 2015 Edition, except where general terms of ordinary dictionary significance are used.

Botanical classification: *Anemone multifida* x *Anemone sylvestris* 'ANEM079'.

Parentage:

*Female, or seed, parent.*—*Anemone multifida* 'Rosea', not patented.

*Male, or pollen, parent.*—Unnamed selection of *Anemone sylvestris*, not patented.

Propagation:

*Type.*—In vitro meristem culture.

*Time to initiate roots, summer.*—About 14 days at temperatures about 25° C.

*Time to initiate roots, winter.*—About 20 days at temperatures about 10° C.

*Time to produce a rooted young plant, summer.*—About 60 days at temperatures about 20° C.

*Time to produce a rooted young plant, winter.*—About 75 days at temperatures about 18° C.

*Root description.*—Medium in thickness, fleshy; close to N199C to N199D in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous perennial; upright habit with leaves developing from basal rosettes; numerous basal rosettes developing per plant; narrowly oblong to ovate in overall shape; moderately vigorous growth habit; moderate growth rate.

*Plant height, soil level to top of foliar plane.*—About 47.6 cm.

*Plant height, soil level to top of floral plane.*—About 53.5 cm.

*Plant diameter.*—About 29.6 cm.

Branch description:

*Number of primary branches per plant.*—About 25.

*Number of secondary branches per plant.*—About 35.

*Length, primary branches.*—About 23.7 cm.

*Diameter, primary branches.*—About 3.5 mm.

*Internode length, primary branches.*—About 11.4 cm.

*Strength.*—Strong.

*Aspect.*—Mostly upright.

*Texture and luster.*—Densely pubescent; moderately glossy.

*Color, developing.*—Close to 144B; distally, close to 148A.

*Color, developed.*—Close to 144B to 144C.

Leaf description:

*Arrangement, basal leaves.*—Alternate; simple.

*Arrangement, cauline leaves.*—Whorled or opposite; simple.

*Length, basal leaves.*—About 8.4 cm.

*Width, basal leaves.*—About 9.8 cm.

*Length, cauline leaves.*—About 6.2 cm.

*Width, cauline leaves.*—About 8.5 cm.

*Shape, basal leaves.*—Roughly orbicular to reniform in outline; palmately cleft.

*Shape, cauline leaves.*—Roughly reniform in outline; palmately cleft.

*Apex, basal and cauline leaves.*—Acute.

*Base, basal leaves.*—Hastate.

*Base, cauline leaves.*—Attenuate.

*Margin, basal and cauline leaves.*—Laciniate with incised to serrate margins; depth of sinuses are deep and divergent.

*Texture and luster, basal and cauline leaves, upper surface.*—Sparsely pubescent, not rugose; slightly glossy.

*Texture and luster, basal and cauline leaves, lower surface*.—Moderately pubescent, not rugose; matte.

*Venation pattern, basal and cauline leaves*.—Laciniate.

*Color, basal leaves*.—Developing leaves, upper surface: Close to 144A to 144B. Developing leaves, lower surface: Close to 144B. Fully expanded leaves, upper surface: Close to 137B; venation, close to 144B. Fully expanded leaves, lower surface: Close to 147B; venation, close to 144B.

*Color, cauline leaves*.—Developing leaves, upper surface: Close to 144A to 144B. Developing leaves, lower surface: Close to 144B. Fully expanded leaves, upper surface: Close to between NN137A and 147A; venation, close to 144B. Fully expanded leaves, lower surface: Close to 147B; venation, close to 144B.

*Leaf petioles*.—Length, basal leaves: About 23.4 cm. Diameter, basal leaves: About 2 mm. Length, cauline leaves: About 3.4 cm. Diameter, cauline leaves: About 2 mm to 2.5 mm. Strength, basal and cauline leaves: Strong. Texture and luster, basal and cauline leaves, upper and lower surfaces: Sparsely to moderately pubescent; slightly glossy. Color, basal and cauline leaves, upper surface: Close to 144B. Color, basal and cauline leaves, lower surface: Close to 144B.

Flower description:

*Flower arrangement and flowering habit*.—Solitary single-type rotate flowers; freely flowering habit with 60 flowers developing per plant; flowers face mostly upright.

*Fragrance*.—None detected.

*Natural flowering season*.—Plants of the new *Anemone* begin flowering about ten weeks after planting and flower from early spring to the late spring in The Netherlands.

*Flower longevity*.—Individual flowers last about ten days on the plant; flowers not persistent.

*Flower diameter*.—About 4.1 cm.

*Flower length* (*depth*).—About 1 cm.

*Flower buds*.—Length: About 1 cm. Diameter: About 8 mm. Shape: Ovate. Texture and luster: Densely pubescent; matte. Color: Close to 71A to 71B; towards the base, close to 146D.

*Petals*.—Absent.

*Sepals*.—Quantity and arrangement: About five, and occasionally six, arranged in a single whorl. Length: About 2.2 cm. Width: About 1.3 cm to 1.4 cm. Shape: Ovate to elliptic; slightly concave. Apex: Obtuse. Base: Cuneate. Margin: Entire. Texture and luster, upper surface: Smooth, glabrous; moderately velvety; matte. Texture and luster, lower surface: Densely pubescent; slightly glossy. Color: When opening, upper surface: Close to NN78B. When opening, lower surface: Close to 70B. Fully opened, upper surface: Close to NN78C; towards the margins, close to NN78D; venation, similar to lamina colors; color does not change with development. Fully opened, lower surface: Close to 70A to 70B; venation, similar to lamina colors; color does not change with development.

*Peduncles*.—Length: About 13 cm to 25 cm. Diameter: About 2 mm. Aspect: Mostly upright. Strength: Strong. Texture and luster: Moderately pubescent; slightly glossy. Color: Close to 144A; distally, close to 148A.

*Reproductive organs*.—Androecium: Stamen number per flower: About 100. Filament length: About 5 mm. Filament color: Close to 154D. Anther shape: Oblong. Anther length: About 1 mm. Anther diameter: About 0.5 mm. Anther color: Close to 153C to 153D. Amount of pollen: Scarce. Pollen color: Close to 21B. Gynoecium: Pistil number per flower: About 175. Pistil length: About 1 mm. Stigma shape: Club-shaped. Stigma length: About 0.5 mm. Stigma diameter: About 0.5 mm. Stigma color: Close to 177D. Style length: About 0.5 mm. Style color: Close to 177B. Ovary color: Close to 143B.

*Seeds and fruits*.—To date, seed and fruit development have not been observed on plants of the new *Anemone*.

Garden performance: Plants of the new *Anemone* have been observed to have good garden performance, to tolerate high temperatures of about 35° C. and to be suitable for USDA Hardiness Zones 4 through 9.

Pathogen & pest resistance: To date, plants of the new *Anemone* have not been observed to be resistant to pathogens and pests common to *Anemone* plants.

It is claimed:

1. A new and distinct *Anemone* plant named 'ANEM079' as illustrated and described.

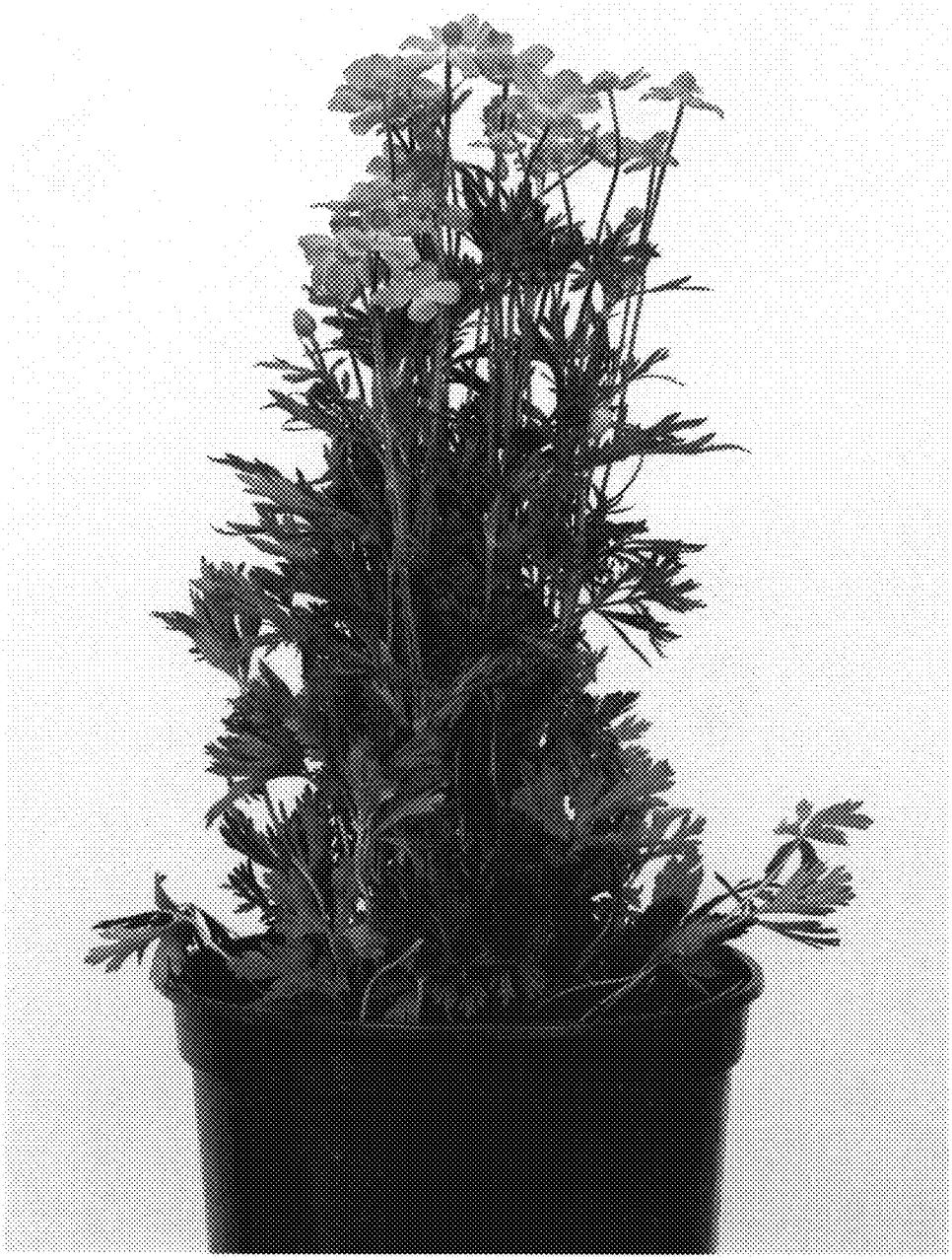

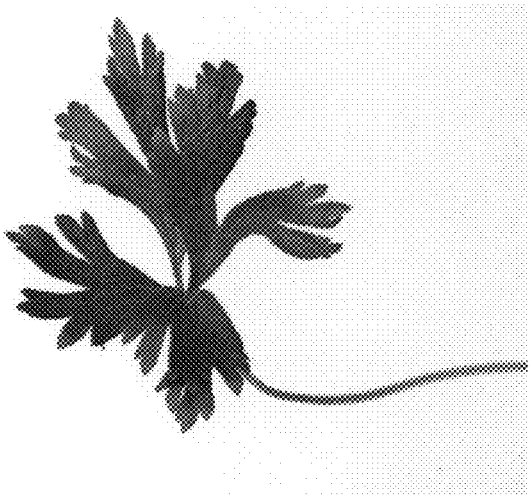
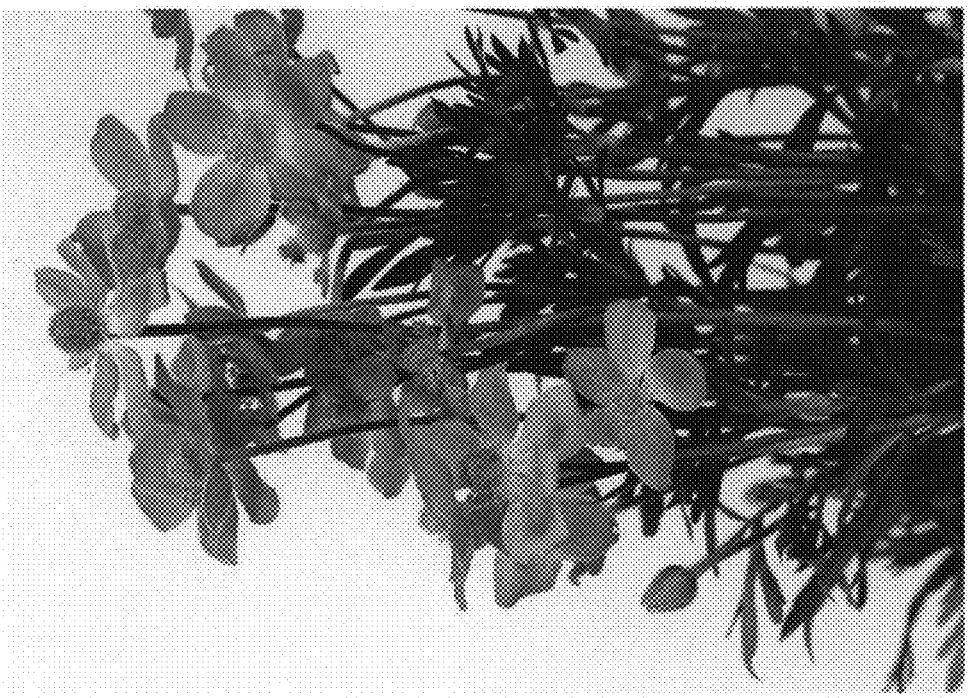

* * * * *